United States Patent [19]

May et al.

[11] Patent Number: 5,376,691
[45] Date of Patent: Dec. 27, 1994

[54] AUTOMATICALLY ADMIXABLE MEDIUM FOR MAKING TEMPORARY CROWNS AND BRIDGES

[75] Inventors: Ulrich May, Halstenbek; Jürgen Engelbrecht, Hamburg; Ernst Mühlbauer, Hamburg; Edgar Lein, Hamburg, all of Germany

[73] Assignee: Ernst Mühlbaner KG, Hamburg, Germany

[21] Appl. No.: 24,051

[22] Filed: Mar. 1, 1993

[30] Foreign Application Priority Data

Apr. 3, 1992 [DE] Germany .................. 4211040

[51] Int. Cl.⁵ ................. C08J 3/18; C08K 3/34; C08K 5/54
[52] U.S. Cl. ........................ 522/77; 522/79; 522/80; 522/81; 522/83; 522/65; 522/14; 522/908; 523/115; 523/116; 523/117
[58] Field of Search ............. 523/117, 116, 115; 522/24, 908, 81, 79, 77, 65, 140, 80, 83

[56] References Cited

U.S. PATENT DOCUMENTS

| | | | |
|---|---|---|---|
| 4,372,836 | 2/1983 | Schmitt et al. | 522/71 |
| 4,389,497 | 6/1983 | Schmitt et al. | 523/116 |
| 4,503,169 | 3/1985 | Randkev | 523/117 |
| 4,544,359 | 10/1985 | Waknine | 523/115 |
| 4,696,955 | 9/1987 | Kuhlmann | 522/77 |
| 4,707,504 | 11/1987 | Walkowiak et al. | 523/116 |
| 4,721,735 | 1/1988 | Bennett et al. | 522/71 |
| 4,767,798 | 8/1988 | Gasser et al. | 523/117 |
| 4,820,744 | 4/1989 | Kubota et al. | 522/908 |
| 4,906,446 | 3/1990 | Engelbrecht et al. | 523/109 |
| 5,004,501 | 4/1991 | Faccioli et al. | 523/117 |
| 5,130,348 | 7/1992 | Zahler et al. | 523/109 |

*Primary Examiner*—Susan W. Berman
*Attorney, Agent, or Firm*—Keil & Weinkauf

[57] ABSTRACT

The invention describes a material for making temporary crowns and bridges that comprises two pastes and can be mixed in a static mixer/application in one cycle without the incorporation of bubbles, and can be easily pressed out. The polymers produced from this are aesthetically pleasing and remarkably break-resistant. Their polymerization-related shrinkage proves to be extremely low. Their radiopaqueness meets clinical requirements.

9 Claims, No Drawings

AUTOMATICALLY ADMIXABLE MEDIUM FOR MAKING TEMPORARY CROWNS AND BRIDGES

The invention relates to a temporary crown and bridge material comprising two pastes that can be mixed in a static mixer/applicator in one cycle and easily pressed out.

Temporary crown and bridge materials are used to make a crown or bridge for patients who will only wear it for a short period of time.

Typically these materials comprise a liquid/powder combination that is mixed together. The liquid in this combination is essentially composed of a monofunctional monomer (methyl methacrylate, for example) and an activator; the powder comprises a polymer (polymethyl methacrylate, for example) and a catalyst.

Systems of this type are easy to handle, and the crowns and bridges produced from them are remarkably break-resistant.

The liquids are, however, not without problems. They evaporate easily and have an unpleasant odor. In addition, during polymerization these systems have a potentially pulp-damaging heat build-up and a strong tendency to shrink.

More sophisticated materials therefore comprise two pastes that contain difunctional methacrylates and fillers, as well as an activator and a catalyst that are distributed separately to the pastes.

They can be mixed together simply, have a negligible odor, and have a clearly better shrinking behavior and lower heat build-up during hardening.

A large problem, however, is that numerous air bubbles can be incorporated during mixing on the mixing block, which later leads to rough spots and strong discolorations in the hardened material. Furthermore, because of their hardness, these materials are very brittle and tend to break easily.

The object of the invention, therefore, was to find a temporary crown and bridge material that comprises two pastes, can be mixed free from bubbles and does not have the aforementioned brittleness.

Surprisingly, it has now been demonstrated that temporary crown and bridge materials that meet these requirements can be obtained when they are characterized in that a) one comprises a paste of difunctional acrylates, activators and a radiopaque filler;

b) the second paste comprises a non-polymerizable (inert) softener, a catalyst and a structure former;

c) the mixture ratio of the pastes in accordance with a) and b) is between 20:1 and 5:1; and that d) both pastes have a rheological behavior such that both pastes can be mixed in a static mixer/applicator in one cycle and easily pressed out.

Such materials mixed in this way can be inserted directly into a prepared impression taken beforehand for the purpose of application to the tooth stump in the mouth. There they polymerize while hardening, and can subsequently be shaped further.

The temporary crowns and bridges produced in this way are produced to be free from bubbles, aesthetically pleasing and remarkably break-resistant. Polymerization-related shrinkage also proves to be extremely low. The radiopaqueness meets clinical requirements.

Suitable pastes in accordance with a) contain difunctional acrylates such as bisphenol-A-glycidyl diacrylate, bisphenol-A-diglycidyl diacrylate, triethylene glycol diacrylate, hexanediol diacrylate, urethane diacrylate and the like.

Tertiary amines such as triethanol amine, dimethyl aminobenzoic acid ester, dihydroxyethyl toluidine, copper naphthenate and the like are suitable as activators.

Bisphenol-A-diglycidyl diacrylate has proven to be a particularly suitable difunctional acrylate, and dimethyl-p-toluidine has proven to be a particularly suitable activator.

Powders of insoluble glasses containing suitable quantities of heavy metals such as yttrium, zirconium or lanthanum are suitable as radiopaque fillers. Particularly satisfactory aesthetic results and good radiopaqueness are obtained with barium and/or strontium glasses.

Suitable pastes in accordance with b) contain softeners that, for the sake of flexibility, cannot be polymerized along with the other components but, on the other hand, are sufficiently insoluble in the milieu of the mouth. Liquid paraffins, long-chain glycols and inert alkylphthalates are suitable. Medium-molecular-weight polyethylene glycols such as polyethylene glycol-200 or polyethylene glycol-400 are particularly suitable.

Suitable catalysts include peroxides, such as dibenzoyl peroxide, methyl ethyl ketone peroxide, cumene hydroperoxide and malonyl sulfamides, as described in European Patent 0,059,451, or autooxidatively acting CH-active compounds, as described in "Makromolekulare Chemie" (Macromolecular Chemistry) 99 (1966), pp. 96–102.

The use of bis-dichlorobenzoyl peroxide as a catalyst particularly suitable.

The systems can additionally be light-curable, as described in U.S. Pat. No. 4,071,424 or German Patent 3,136,484.

Amorphous silicon dioxide modifications are advantageous structure formers. Examples are pyrogens and precipitated silicic acids such as diatomaceous earth.

Agglomerated pyrogenic silicic acids or sintered silica gel, as described in European Patents 0,040,232 and 0,113,926, are particularly suitable.

Such fillers have little tendency to thicken later and have the property that their thixotropic behavior is uniform and is scarcely dependent on the storage length of the pastes.

As a result, a durable, consistent mixing result can be assured. Also, the pressure used in pressing out the material, which muse be carefully controlled, can be held constant.

The quantity ratio of the pastes to be mixed can vary within a range between 20:1 and 5:1 (paste in accordance with a) to paste in accordance with b)). Within these ranges, the added softener leads to particularly favorable break-resistant materials.

Outside of these limits the materials have too little flexibility and are brittle or much too soft and instable in the milieu of the mouth.

Finally, the theological behavior of the two pastes must be considered. It is known to mix two liquids or pastes with the same or similar consistencies and equal quantity ratios in static mixers. It is, however, in the nature of the materials in accordance with the invention that they require a different mixture ratio. It was found, however, that a mixture having a ratio of approximately 10:1 can lead to a satisfactory mixing result only when the consistency of the paste added in the smaller amount is adjusted to be thinner. Satisfactorily thorough mixing of pastes of identical or similar consistencies cannot be achieved solely by means of a special design of the static mixer, because the pastes must have a minimum stability appropriate for the intended application, because the size of the mixer is limited for economic reasons, and because the mixing time must be very short for technical reasons, given the intended application.

In order to attain the desired consistency, the acrylates of the first paste a) are selected so that their viscosity is below 500 cp. The softeners of the second paste b) must be selected so that their viscosity is below that of the acrylates mentioned above. To achieve the minimum stability required for the intended application without decreasing the ability of the mixer to function, agents for increasing stability, such as pyrogenic silicic acid, should also be added.

It is particularly easy to handle the materials. Once a hollow mixing needle has been attached to a mixer/applicator, as described in European Patents 0,232,733 and 0,261,466, all that has to be done is to operate a feeder. The material emerges from the mixer homogeneously mixed and in exactly the right mixing ratio. The pastes, which were previously bubble-free, are still bubble-free after mixing and therefore yield bubble-free polymers. The crowns and bridges produced in this manner are aesthetically pleasing and remarkably break-resistant.

Their polymerization-related shrinkage proves to be extremely low. Their radiopaqueness meets the clinical requirements.

The example illustrated below is intended to describe a material in accordance with the invention.

EXAMPLE

The following components are stirred together to form a catalyst paste:

| polyethylene glycol-400 | 48.0 weight % |
|---|---|
| dibutyl phthalate | 12.0 weight % |
| dichlorodibenzoyl peroxide | 8.0 weight % |
| sintered silica gel | 32.0 weight % |

Accordingly, the following components are stirred together to form a basic paste:

| bisphenol-A-diglycidyl diacrylate | 50.0 weight % |
|---|---|
| tripropylene glycol diacrylate | 7.0 weight % |
| strontium glass, silanized | 39.0 weight % |
| silanized pyrogenic silicic acid | 3.0 weight % |
| dimethyl-p-toluidine | 1.0 weight % |
| hydroquinone monomethyl ether | 0.01 weight % |
| iron oxide pigment | 0.02 weight % |

The basic paste and the catalyst paste are filled separately into the chambers of a double cartridge corresponding to European Patent 0,261,466; the double cartridge is provided with a hollow mixing needle and, with the use of a discharging device corresponding to European Patent 0,232,733, the pastes are directly applied by means of the hollow mixing needle into an impression taken beforehand. Afterwards the impression, including the mixed material, is immediately applied to a prepared tooth stump. After three minutes the impression can be removed. The hardened crown remaining on the tooth stump is lifted out and worked on outside of the mouth.

After polishing, a bubble-free crown is obtained that is very aesthetically pleasing and highly break-resistant.

We claim:

1. A radiopaque material for making temporary crowns and bridges, comprising a mixture of two pastes, wherein;
   a) a first paste comprises difunctional acrylates, activators and a radiopaque filler;
   b) a second paste, containing no substances having active double bonds, comprises a catalyst, a modified silicon dioxide structure former, made of agglomerated pyrogenic silicic acid or sintered silica gel, and a softener that cannot be polymerized along with the other components but is sufficiently insoluble in the mouth, selected from the group consisting of liquid paraffins, long-chain glycols and inert alkylphthalates;
   c) the mixture ratio of the pastes a) and b) is between 20:1 and 5:1; and
   d) both pastes have a rheological behavior such that both pastes can be mixed in a static mixer/applicator in one cycle and easily pressed out.

2. The material as defined by claim 1, wherein the difunctional acrylate is bisphenol-A-diglycidyl acrylate.

3. The material as defined by claim 1, wherein the activator is dimethyl-p-toluidine.

4. The material as defined by claim 1, wherein the radiopaque filler is barium and/or strontium glass.

5. The material as defined by claim 1, wherein the non-polymerizable softener is polyethylene glycol-200 or polyethylene glycol-400.

6. The material as defined by claim 1, wherein the catalyst is bis-dichlorobenzoyl peroxide.

7. The material as defined by claim 1, wherein, in addition, it is light-curable.

8. The material as defined by claim 1, wherein the mixture ratio of the pastes in accordance with a) and b) is 10:1.

9. A procedure wherein a material as defined in claim 1 is mixed in a static mixer/applicator and is pressed out from it.

* * * * *